United States Patent [19]

Fried

[11] Patent Number: 5,136,101
[45] Date of Patent: Aug. 4, 1992

[54] PROCESS FOR THE PREPARATION OF KETONES

[75] Inventor: Herbert E. Fried, Houston, Tex.

[73] Assignee: Shell Oil Company, Houston, Tex.

[21] Appl. No.: 769,072

[22] Filed: Sep. 30, 1991

[51] Int. Cl.$^5$ ............................................. C07C 45/29
[52] U.S. Cl. ..................................................... 568/402
[58] Field of Search ........................................ 568/402

[56] References Cited

U.S. PATENT DOCUMENTS 4,620,033 10/1986 Isshiki et al. ...................... 562/519

FOREIGN PATENT DOCUMENTS 5096516 11/1986 Japan .

OTHER PUBLICATIONS

Cella et al, J. Org. Chem., vol. 40, pp. 1860–1862 (1975).
Miyazawa et al., "Oxidation of Benzyl Alcohol with Iron(III) Using Polymers Containing Nitroxyl Radical Structure as a Mediator", J. Polym. Sci., Polym. Chem. Ed., 23(9), 1985, pp. 2487–2494.
Grigor'ev et al., "Participaton of Nitroxyl Radical in the Oxidation of Aldehyde and Alcohol Groups in 3-imidazolin-1-oxyls", Izc. AKad. Nauk SSSR, Ser. Khim., (1), 1978, pp. 208–210.
Miyazawa et al., "Oxidation of Benzyl Alcohol with Copper(II) Mediated by a Polymeric Oxoaminium Salt," J. Mol. Catal., 49(1), 1988, 131–134.
Ganem et al., "Biological Spin Labels as Organic Reagents. Oxidation of Alcohols to Carbonyl Compounds Using Nitroxyls," J. Org. Chem., 40(13), 1975, pp. 1998–2000.
Miyazawa et al., "Oxidaton of Benzyl Alcohol by Iron(III) Mediated by Nitroxyl Radical," J. Mol. Catal., 31(2), 1985, pp. 217–220.
Anelli et al., "Fast and Selective Oxidation of Primary Alcohols to Aldehydes or to Carboxylic Acids and of Secondary Alcohols to Ketones Mediated by Oxoammonium Salts under Two-Phase Conditions," J. Org. Chem., 52 (12), pp. 2559–2562.
Inokuchi et al., "A Selective and Efficient Method for Alcohol Oxidations Mediated by N-Oxoammonium Salts in Combination with Sodium Bromite," J. Org. Chem., 1990, 55, pp. 462–466.
Organic Synthesis, vol. 69, p. 212 (1990).
Semmelhack et al., "Oxidation of Alcohols to Aldehydes with Oxygen and Cupric Ion, Mediated by Nitrosonium Ion," J. Am. Chem. Soc. 1984, 106, 3374–3376.
Yamaguchi et al., "Application of Redox System Based on Nitroxides to Organic Synthesis," Pure & Applied Chemistry, vol. 62(2), 1990, pp. 217–222.

*Primary Examiner*—James H. Reamer
*Attorney, Agent, or Firm*—Pamela J. McCollough

[57] ABSTRACT

A process for the preparation of a ketone which comprises reacting the corresponding secondary alkanol with a solubilized stable free radical nitroxide having the formula:

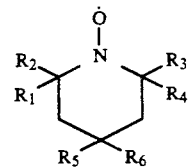

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, and an alkali metal nitrosodisulfonate in the presence of an oxidant at a temperature in the range of from about $-10°$ C. to about 80° C. and thereafter separating out the ketone.

18 Claims, No Drawings

PROCESS FOR THE PREPARATION OF KETONES

FIELD OF THE INVENTION

This invention relates to a process for the preparation of ketones by the oxidation of the corresponding secondary alcohols in the presence of a stable free radical nitroxide, an alkali metal nitrosodisulfonate and an oxidant.

BACKGROUND OF THE INVENTION

It is known to use nitroxyl radicals/oxoammonium salts in the oxidation of primary alcohols to produce aldehydes and acids, and the oxidation of secondary alcohols to produce ketones (*Journal of Organic Chemistry*, vol. 52 (12), pp. 2559-2562 and *Journal of Organic Chemistry*, vol. 55, 1990, pp. 462-466).

It is reported in the open literature that primary aliphatic alcohols can be converted to aldehydes, but only in 30-40% yields in the presence of catalytic amounts of cuprous chloride, 2,2,6,6,-tetramethylpiperidine-1-oxyl, and atmoshperic oxygen (*Journal of American Chemical Society*, 1984, 106. pp. 3374). It is also known that higher yields of aldehydes can be obtained if stoichiometric amounts of cupric or ferric salts are used instead of catalytic amounts of the cuprous salts (*Pure and Applied Chemistry*, vol. 62(2), 1990, pp. 217-222).

OBJECTS OF THE INVENTION

It is an object of this invention to produce ketones in high yields and/or high selectivities from secondary alkanols.

It has been found that ketones can be produced in high yields and/or with high selectivities by using catalytic amounts of a stable free radical nitroxide, an alkali metal nitrosodisulfonate and an oxidant.

SUMMARY OF THE INVENTION

This invention relates to a process for the preparation of a ketone which comprises reacting the corresponding secondary alkanol with a solubilized stable free radical nitroxide having the formula:

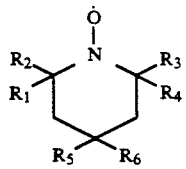

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, and an alkali metal nitrosodisulfonate in the presence of an oxidant at a temperature in the range of from about $-10°$ C. to about 80° C. and thereafter separating out the ketone.

DESCRIPTION OF THE PREFERRED EMBODIMENTS

The present process converts secondary alkanols to the corresponding ketones by contacting the secondary alkanol with a solubilized stable free radical nitroxide and an alkali metal nitrosodisulfonate in the presence of an oxidant at a temperature in the range of from about $-10°$ C. to about 80° C.

The secondary alkanol reactant suitably comprises one or more secondary alkanols having a carbon number in the range of from about 3 to about 45. An alkanol consisting essentially of secondary, mono-alkanols is preferred. Most preferably, the alkanol reactant consists essentially of one or more $C_6$ to $C_{30}$ secondary mono-alkanols. Preference can also be expressed for secondary alkanols having from 8 to about 22 carbon atoms, with $C_9$ to $C_{18}$ secondary alkanols considered more preferred and $C_{11}$ to $C_{18}$ secondary alkanols considered most preferred. As a general rule, the carbon chains of the secondary alkanols may be of either branched or linear (straight-chain) structure, although preference further exists for alkanol reactants in which greater than about 50 percent, more preferably greater than about 70 percent and most preferably greater than about 90 percent of the molecules are of linear (straight-chain) carbon structure. In large part, such preferences relate more to the utility and value of the products than to the operability or performance of the process of the invention.

The general suitability of such secondary alkanols as reactants in oxidation reactions is well recognized in the art. Examples of specific secondary alkanols and of commercially available alkanols and alkanol mixtures within this class are also well known. Commercially available mixtures of secondary mono-alkanols prepared via the oxidation of paraffins, and from internal olefins and alpha-olefin mixtures, via sulfation and hydrolysis reactions are particularly suitable.

Suitable examples of $C_{10}$ to $C_{20}$ secondary alkanols for use in the present invention which are commercially available include Tergitol 15, a trademark of and sold by Union Carbide in which the main components are $C_{11}$ to $C_{15}$ compounds; Tergitol 45, in which the main components are $C_{14}$ to $C_{15}$ compounds; Softanol 24, a trademark of and sold by Nippon Shokubai Kagaku Kogyo Co., Ltd., in which the main components are $C_{12}$ to $C_{14}$ compounds, and the like. Examples of suitable secondary alkanols having lower carbon numbers include isopropanol, 2-butanol, 2-pentanol, 3-pentanol, 2-hexanol, 3-hexanol, 2-octanol, 3-octanol and the like.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the presursor to a stable free radical from which the stable free radical may be produced in situ.

The stable free radical nitroxides, as used in the present process, are precursors to catalysts, i.e., oxoammonium salts, active for the oxidation of secondary alkanols to the corresponding ketones. These catalysts are generated in situ by the oxidation of a stable free radical nitroxide to an oxoammonium salt with an oxygen-containing oxidant. The stable free radical nitroxide can be obtained by the oxidation of secondary amines or hydroxylamines.

The stable free radical nitroxides which are suitable for use in the instant invention have the formula:

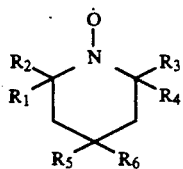

wherein each of $R_1$, $R_2$, $R_3$ and $R_4$ is an alkyl, aryl or heteroatom substituted alkyl group having 1 to about 15 carbon atoms and no hydrogen is bound to the remaining valences on the carbon atoms bound to the nitrogen, and each of $R_5$ and $R_6$ is alkyl, hydrogen, aryl or a substituted heteroatom. As used herein, the term "alkyl" is meant to include cycloalkyl. The alkyl (or heteroatom substituted) groups $R_1-R_4$ may be the same or different, and preferably contain 1 to 15 carbon atoms. Preferably, $R_1-R_4$ are methyl, ethyl, or propyl groups. In addition to hydrogen, the heteroatom substituents may include, halogen, oxygen, nitrogen and the like. Preferably, one of $R_5$ and $R_6$ is hydrogen with the other being a substituted heteroatom which does not interfere with the reaction. Suitable substituted heteroatoms include —OR,

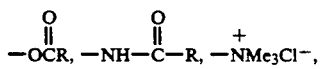

—O—$SO_3H$, —O—polymer and the like.

In a preferred embodiment, the nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof, with 2,2,6,6-tetramethyl-piperidine-1-oxyl, 2,2,6,6-tetramethyl-piperidine-1-oxyl-4-sulfate, and 4-alkoxy-2,2,6,6-tetramethyl-piperidine-1-oxyl being particularly preferred.

The alkali metal nitrosodisulfonate reactant may suitably be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate is typically added to the reaction mixture as a solid although it can be mixed with water prior to being added to the other reactants. While not wishing to be bound by any particular theory, it is believed that the alkali metal nitrosodisulfonate decomposes under the reaction conditions. One or more of these decomposition products appears, in the presence of an oxidant, to become an oxidant which is capable of oxidizing the nitroxide to an oxoammonium salt. It is believed that nitrogen oxides ($NO_x$) are generated in the reaction and are the active species.

The oxidants suitable for use in the instant invention are those compounds which are capable, in conjunction with the nitrosodisulfonate species, of oxidizing the stable free radical nitroxide to the oxoammonium salt. Suitable oxidants include oxygen or an oxygen-containing gas such as air. Whereas pure oxygen is preferred to accomplish the desired conversion, the oxygen can also be diluted with an inert gas such as nitrogen, helium, argon, or other similar gas. While air can be used as the oxidant, the reaction rate is slower. For purposes of increasing the reaction rate, higher $O_2$ pressures such as, for example, 1000 psi can also be utilized. In a preferred embodiment, pure oxygen is used as the oxidant and it is bubbled into the reaction solution at atmospheric pressure. In another embodiment, oxygen can be bubbled initially through the reaction solution in order to commence the reaction and then the flow of oxygen can be stopped without stopping the reaction.

The amounts and concentrations of the reactants utilized in the process of the instant invention can vary within wide ranges. The amount of stable free radical nitroxide is typically in the range of from about 1 mole percent about 50 mole percent, preferably from about 5 mole percent to about 20 mole percent, basis the number of moles of starting secondary alkanol. Generally, the amount of an alkali metal nitrosodisulfonate utilized will be in the range of from about 1 mole percent to about 35 mole percent, preferably from about 10 mole percent to about 20 mole percent, basis the number of moles of the starting secondary alkanol.

The reaction in the instant invention is carried out utilizing a solubilized stable free radical nitroxide. The solvent is typically one in which the secondary alkanol is readily soluble. Solvents which are most suitable are those which are inert in the reaction. In general, faster reaction rates are observed when solvents having dielectric constants greater than about 20 are used. The solvent may be added to the reaction mixture or, alternatively, the nitroxide may be dissolved in the solvent prior to addition of the nitroxide to the reaction medium. The solvent is typically selected from the group consisting of acetonitrile, tertiary alcohols such as tertiary butyl alcohol or tertiary amyl alcohol, ethyl acetate, sulfolane, dichloromethane and mixtures thereof, with tertiary butyl alcohol and acetonitrile being preferred. The amount of solvent utilized in the process is generally from about 20:1 to about 0.5:1, preferably from about 15:1 to about 5:1, basis the weight of the starting secondary alkanol.

The process of the present invention is typically conducted under mild conditions, with good results being obtained using a temperature in the range of from about $-10°$ C. to about 80° C., preferably about 25° C. to about 50° C., and more preferably, from about 30° C. to about 40° C. In general, the higher the temperature, the less time it takes the reaction to proceed to completion. Reaction pressures are not critical although higher pressures result in increased reaction rates. Pressures in the range of from about atmospheric pressure up to about 1000 psig $O_2$ can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.032 moles of secondary alkanol, 0.006 moles of the nitroxide, 0.0075 moles of an alkali metal nitrosodisulfonate which has been disolved in water and solvent may be added to the reaction vessel, followed by bubbling an $O_2$ stream through the reaction mixture. Alternatively, the secondary alkanol, the alkali metal nitrosodisulfonate and solvent may be added to the reaction vessel and allowed to reach equilibrium, followed by the dropwise or immediate addition of 10 mole percent of the nitroxide which has been dissolved in a minimum amount of solvent. In a preferred embodiment, the reaction is carried out by adding the solvent, the secondary alkanol, the nitroxide, the water and then the alkali metal nitrosodisulfonate together and then bubbling an oxidizing gas through the mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. The reaction product can be purified by a number of conventional means such as distillation or other methods known in the art.

Depending upon process conditions the solvent utilized and the concentration of the nitroxide, the yields of ketones obtained by this invention can be greater than about 80% of starting secondary alkanol material being converted. The products produced by the instant process can be used in a variety of applications. For example, these products can be used as solvents or as intermediates to produce amines or ethers.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

Example 1

4.2 Grams of 2-octanol, 1.0 gram of 2,2,6,6-tetramethyl-piperidine-1-oxyl, 50 milliliters of acetonitrile and 2 grams of water were charged to a 100 milliter round bottomed flask. To this mixture was added 2 grams of potassium nitrosodisulfonate. An $O_2$ stream was then bubbled through this solution. The reaction was held at a temperature of 35° C. over a 4 hour period. The results are presented in Table I.

Example 2

4.2 Grams of 2-octanol, 0.3 grams of 2,2,6,6-tetramethyl-piperidine-1-oxyl, 50 milliliters of acetonitrile and 2 grams of water were charged to a 100 milliter round bottomed flask. To this mixture was added 2 grams of potassium nitrosodisulfonate. An $O_2$ stream was then bubbled through this solution. The reaction was held at room temperature over a 16 hour period. The results are presented in Table I.

Example 3

4.2 Grams of 2-octanol, 1 gram of 2,2,6,6-tetramethyl-piperidine-1-oxyl, added 50 milliliters of sulfolane and 2 grams of water were charged to a 100 milliter round bottomed flask. To this mixture was added 2 grams of potassium nitrosodisulfonate. An $O_2$ stream was then bubbled through this solution. The reaction was held at a temperature of 35° C. over a 4 hour period. The results are presented in Table I.

Example 4

4.2 Grams of 2-octanol, 1 gram of 2,2,6,6-tetramethyl-piperidine-1-oxyl, 50 milliliters of acetonitrile and 2 grams of water were charged to a 100 milliter round bottomed flask. To this mixture was added 2 grams of potassium nitrosodisulfonate. An $O_2$ stream was then bubbled through this solution. The reaction was held at a temperature of 60° C. over a 2 hour period. The results are presented in Table I.

Example 5

4.2 Grams of 2-octanol, 1 gram of 2,2,6,6-tetramethyl piperidine-1-oxyl, 50 milliliters of dichloromethane and 2 grams of water were charged to a 100 milliliter round bottomed flask. To this mixture was added 2 grams of potassium nitrosodisulfonate. An $O_2$ stream was then bubbled through this solution. The reaction was held at a temperature of 35° C. over a 4 hour period. The results are presented in Table I.

Comparative Example A

Comparative Example A was carried out in a manner similar to Example 1 except that no nitroxide was used and 25 milliliters of acetonitrile was used. The results are presented in Table I.

Comparative Example B

Comparative Example B was carried out in a manner similar to Example 1 except that no alkali metal nitrosodisulfonate was used.

As can be seen in Table I, both the nitroxide and the alkali metal nitrosodisulfonate are essential for the oxidation of the secondary alkanol to ketones.

TABLE I

| Oxidation Of Secondary Alkanols to Ketones | | |
|---|---|---|
| | % Weight Starting Alkanol Remaining | % Weight Ketone |
| Example 1 | 5.8 | 94.2 |
| Example 2 | 32.1 | 67.9 |
| Example 3 | 15.9 | 84.1 |
| Example 4 | 6.9 | 93.1 |
| Example 5 | 93.5 | 6.5 |
| Comparative Example A | 100 | 0 |
| Comparative Example B | 100 | 0 |

What is claimed is:

1. A process for the preparation of a ketone which comprises reacting the corresponding secondary alkanol with a solubilized stable free radical nitroxide having the formula:

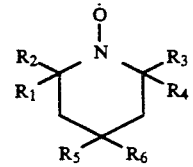

wherein each of $R_1$, $R_2$, $R_3$ and $R_4$ is an alkyl, aryl or heteroatom substituted alkyl group having 1 to about 15 carbon atoms and each of $R_5$ and $R_6$ is alkyl, hydrogen, aryl or a substituted heteroatom, and an alkali metal nitrosodisulfonate in the presence of an oxidant at a temperature in the range of from about −10° C. to about 80° C. and thereafter separating out the ketone.

2. The process of claim 1 wherein the solubilized stable free radical nitroxide is selected from the group consisting of 2,2,6,6-tetramethyl-piperidine-1-oxyl, 4-hydroxy-2,2,6,6-tetramethyl-piperidine-1-oxyl, 4-oxo-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

3. The process of claim 2 wherein the solubilized stable free radical nitroxide is selected from the group consisting of 2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl and mixtures thereof.

4. The process of claim 1 wherein the stable free radical nitroxide is dissolved in a solvent selected from the group consisting of acetonitrile, tertiary butyl alcohol, tertiary amyl alcohol, ethyl acetate, sulfolane, dichloromethane and mixtures thereof.

5. The process of claim 4 wherein the stable free radical nitroxide is dissolved in a solvent selected from the group consisting of tertiary butyl alcohol, acetonitrile and mixtures thereof.

6. The process of claim 1 wherein said alkali metal nitrosodisulfonate is selected from the group consisting of potassium nitrosodisulfonate, sodium nitrosodisulfonate, and mixtures thereof.

7. The process of claim 6 wherein said alkali metal nitrosodisulfonate is potassium nitrosodisulfonate.

8. The process of claim 1 wherein said secondary alkanol is contacted with said solubilized stable free radical nitroxide and said alkali metal nitrosodisulfonate, followed by the addition thereto of said oxidant.

9. The process of claim 8 wherein the amount of solubilized stable free radical nitroxide is in the range of from about 1 mole percent to about 50 mole percent, basis the number of moles of said secondary alkanol.

10. The process of claim 8 wherein the amount of said alkali metal nitrosodisulfonate is in the range of from 1 mole percent to about 35 mole percent, basis the number of moles of said secondary alkanol.

11. The process of claim 1 wherein said secondary alkanol is contacted with said alkali metal nitrosodisulfonate and said oxidant, followed by the addition thereto of said stable free radical nitroxide.

12. The process of claim 11 wherein the amount of solubilized stable free radical nitroxide is in the range of from about 1 mole percent to about 50 mole percent, basis the number of moles of said secondary alkanol.

13. The process of claim 11 wherein the amount of said alkali metal nitrosodisulfonate is in the range of from 1 mole percent to about 35 mole percent, basis the number of moles of said secondary alkanol.

14. The process of claim 1 wherein said oxidant is an oxygen-containing gas.

15. The process of claim 14 wherein said oxygen containing gas is selected from the group consisting of pure oxygen and air.

16. The process of claim 15 wherein said oxygen-containing gas is pure oxygen.

17. The process of claim 1 wherein said process is carried out at a temperature in the range of from about 25° C. to about 50° C. and at atmospheric pressure.

18. The process of claim 17 wherein said process is carried out at a temperature in the range of from about 30° C. to about 40° C. and at atmospheric pressure.

* * * * *